United States Patent
Kovalchuk

(10) Patent No.: US 9,080,950 B2
(45) Date of Patent: Jul. 14, 2015

(54) MULTI-SPECTRAL SCANNING SYSTEM

(75) Inventor: Alexander Kovalchuk, Oxford (GB)

(73) Assignee: ISIS INNOVATION LIMITED, Oxford, Oxfordshire (GB)

( * ) Notice: Subject to any disclaimer, the term of this patent is extended or adjusted under 35 U.S.C. 154(b) by 193 days.

(21) Appl. No.: 13/581,317

(22) PCT Filed: Mar. 8, 2011

(86) PCT No.: PCT/GB2011/050450
§ 371 (c)(1),
(2), (4) Date: Oct. 23, 2012

(87) PCT Pub. No.: WO2011/110839
PCT Pub. Date: Sep. 15, 2011

(65) Prior Publication Data
US 2013/0038741 A1   Feb. 14, 2013

(30) Foreign Application Priority Data

Mar. 9, 2010   (GB) .................................. 1003939.4

(51) Int. Cl.
| | |
|---|---|
| H04N 1/60 | (2006.01) |
| H04N 1/46 | (2006.01) |
| G01N 21/25 | (2006.01) |
| G01J 3/28 | (2006.01) |
| H04N 1/028 | (2006.01) |
| H04N 1/10 | (2006.01) |
| G01N 21/31 | (2006.01) |

(52) U.S. Cl.
CPC ............ *G01N 21/255* (2013.01); *G01J 3/2823* (2013.01); *H04N 1/02865* (2013.01); *H04N 1/1013* (2013.01); *G01N 2021/3174* (2013.01); *G01N 2201/1293* (2013.01)

(58) Field of Classification Search
None
See application file for complete search history.

(56) References Cited

U.S. PATENT DOCUMENTS

| | | | | |
|---|---|---|---|---|
| 4,490,740 | A | 12/1984 | Moriguchi | |
| 5,200,838 | A * | 4/1993 | Nudelman et al. | 358/443 |
| 5,208,674 | A * | 5/1993 | Setchell, Jr. | 348/269 |
| 5,303,165 | A * | 4/1994 | Ganz et al. | 356/319 |
| 5,753,906 | A * | 5/1998 | Gennetten | 250/226 |
| 6,771,400 | B2 * | 8/2004 | Kleiman | 358/505 |
| 7,352,488 | B2 * | 4/2008 | Ben-Chorin et al. | 358/1.9 |
| 7,443,508 | B1 | 10/2008 | Vrhel et al. | |
| 7,708,205 | B2 * | 5/2010 | Kotlarsky et al. | 235/462.24 |

(Continued)

FOREIGN PATENT DOCUMENTS

WO   WO 2004/105380 A1   12/2004

OTHER PUBLICATIONS

Knox, Keith T., "Enhancement of overwritten text in the Archimedes Palimpsest", Proceedings of SPIE, vol. 6810, Jan. 1, 2008, pp. 681004-681004-11.

(Continued)

*Primary Examiner* — Madelein Nguyen
(74) *Attorney, Agent, or Firm* — Withrow & Terranova, P.L.L.C.

(57) ABSTRACT

A method of capturing and processing a multi-spectral image of an object comprises placing the object on a flat-bed scanner (1), using the flat-bed scanner (1) to illuminate the object successively with monochromatic light at a series of wavelengths to produce a plurality of images together forming a composite multi-spectral image, determining a spectral profile of at least a portion of the multi-spectral image and comparing the spectral profile to a stored spectral profile (22, 24).

21 Claims, 2 Drawing Sheets

(56) References Cited

U.S. PATENT DOCUMENTS

| | | | |
|---|---|---|---|
| 8,160,117 B1* | 4/2012 | Courcy | 375/130 |
| 8,936,762 B2* | 1/2015 | Ehrlich et al. | 422/400 |
| 2002/0168784 A1 | 11/2002 | Sundrehagen et al. | |
| 2003/0062422 A1* | 4/2003 | Fateley et al. | 235/494 |
| 2003/0095252 A1 | 5/2003 | Mainberger | |
| 2003/0198364 A1* | 10/2003 | Yonover et al. | 382/103 |
| 2004/0208385 A1* | 10/2004 | Jiang | 382/254 |
| 2004/0208390 A1* | 10/2004 | Jiang et al. | 382/260 |
| 2004/0246477 A1* | 12/2004 | Moon et al. | 356/300 |
| 2005/0286048 A1* | 12/2005 | Kitagawa | 356/318 |
| 2006/0023271 A1* | 2/2006 | Boay et al. | 358/504 |
| 2007/0223058 A1* | 9/2007 | Cotte et al. | 358/474 |
| 2008/0075380 A1* | 3/2008 | Dube et al. | 382/255 |
| 2009/0318815 A1* | 12/2009 | Barnes et al. | 600/473 |
| 2010/0196435 A1* | 8/2010 | Freeman et al. | 424/423 |
| 2011/0090570 A1* | 4/2011 | DeCusatis et al. | 359/619 |
| 2011/0110567 A1* | 5/2011 | Jiang | 382/128 |
| 2011/0125477 A1* | 5/2011 | Lightner et al. | 703/11 |
| 2011/0255745 A1* | 10/2011 | Hodder et al. | 382/103 |
| 2012/0035442 A1* | 2/2012 | Barman et al. | 600/316 |
| 2012/0061590 A1* | 3/2012 | Khojasteh et al. | 250/459.1 |
| 2012/0075647 A1* | 3/2012 | Takahashi | 358/1.9 |
| 2012/0127472 A1* | 5/2012 | Alphonse | 356/456 |
| 2012/0128264 A1* | 5/2012 | Yazdanfar et al. | 382/274 |
| 2012/0219505 A1* | 8/2012 | Wang et al. | 424/9.2 |
| 2013/0015370 A1* | 1/2013 | Damaskinos et al. | 250/459.1 |
| 2013/0148904 A1* | 6/2013 | Wang et al. | 382/224 |
| 2013/0176560 A1* | 7/2013 | Wax et al. | 356/300 |
| 2013/0301883 A1* | 11/2013 | Honeck et al. | 382/112 |
| 2013/0335784 A1* | 12/2013 | Kurtz et al. | 358/3.28 |

OTHER PUBLICATIONS

Kovalchuk, Alexander, "Multispectral imaging of papyri: area segregation by evaluation of their spectral signature correlation," 9th International Conference on Correlation Optics, Oct. 8, 2009; Retrieved from the internet: Proc. of SPIE vol. 7388 738811-1 to 738811-6.

Toque, Jay Arre, et al., "Pigment identification by analytical imaging using multispectral images," Image Processing (ICIP), 2009 16th IEEE International Conference on, IEEE, Piscataway, NJ, USA, Nov. 7, 2009, pp. 2861-2864.

Scholten, J.H., et al. "Hyperspectral imaging—a novel nondestructive analytical tool in pape and writing durability research," Proceedings of Art '05—8th International Conference on Non-Destructive Investigations and Microanalysis for the Diagnostics and Conservation of the Cultural and Environmental Heritage, Jan. 1, 2005.

World Intellectual Property Organization (WIPO), International Search Report and Written Opinion mailed on Aug. 10, 2011 for International Patent Application No. PCT/GB2011/050450 entitled "Multi-Spectral Scanning System".

* cited by examiner

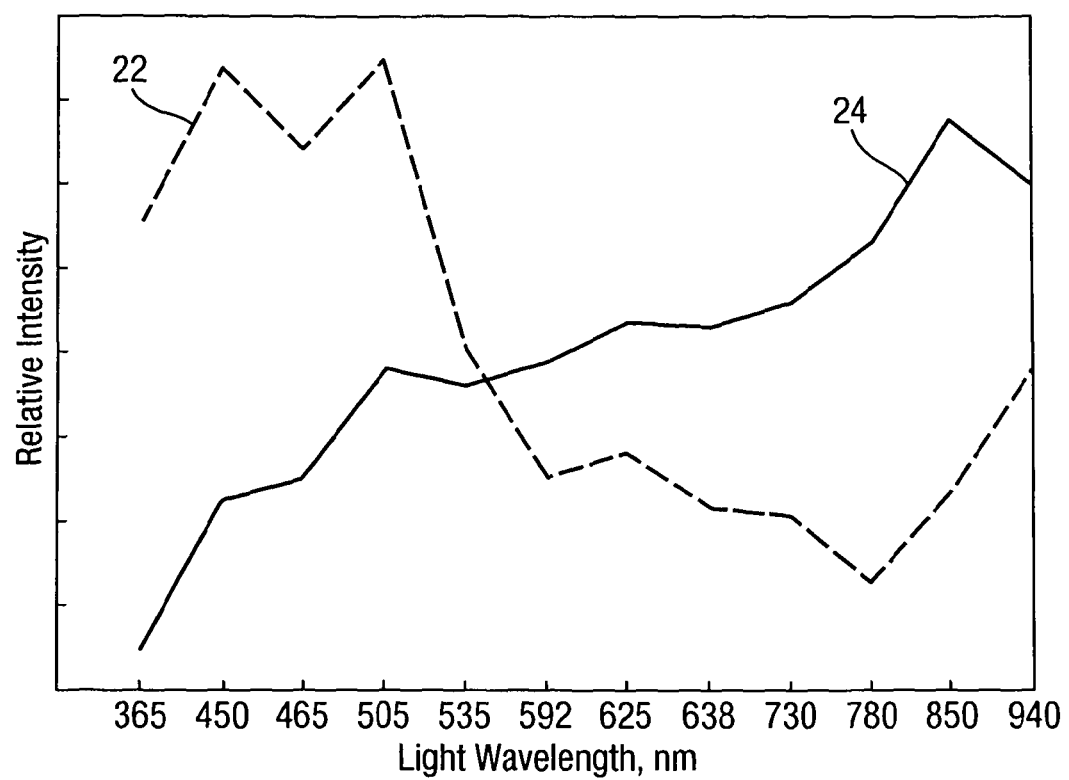

MULTI-SPECTRAL SCANNING SYSTEM

CROSS-REFERENCE TO RELATED APPLICATIONS

This application is filed under the provisions of 35 U.S.C. §371 and claims the priority of International Patent Application No. PCT/GB2011/050450 filed on Mar. 8, 2011, and of Great Britain Patent Application No. 1003939.4 filed on Mar. 9, 2010. The disclosures of the foregoing international patent application and Great Britain patent application are hereby incorporated by reference herein in their respective entireties.

This invention relates to capturing and processing images of historical artefacts and other objects. In relates in particular to systems for multi-spectral imaging.

Historical documents, e.g. papyri that can be up to 3000 years old, are often fragile and faded. This therefore reduces the contrast between the substrate, e.g. papyrus, and the ink, often to levels which make the ink barely visible on the substrate. This low contrast can be due to many different factors such as rubbing or washing off of the ink, or because the whole document has become dirty, e.g. from dirt, silt, carbonisation, oxidation, sunlight, heat, etc.

A technique to analyse these documents in order to reveal the writing on them is therefore required. As well as faded inks and degraded substrates, other complications also exist. For example the substrate may include writings from multiple different authors from different periods which may be in different types of ink. The technique therefore also needs to be able to distinguish between these different inks as well as improving the contrast between the ink and the substrate.

Presently the technique for imaging and analysing such documents is to take multi-spectral images of an artefact using a multi-spectral camera, along with dedicated software to analyse the images. With such apparatus an artefact is illuminated with light and then the image captured by a high definition camera, e.g. a digital camera with a large number of pixels. Typically the artefact is illuminated with a broadband white light source and an interchangeable wavelength filter is placed in front of the lens of the camera to give the required monochromatic image.

By capturing multiple images of the same artefact at different wavelengths, the ability to analyse the artefact is improved since typically some wavelengths will give clearer images than others, depending upon the nature of the artefact and what it is that prevents viewing by the naked eye. Moreover, the relation between intensities of each of the corresponding pixels in these multiple images can be used for multi-spectral image processing and lead to even clearer quality images.

However the inventors have appreciated that there are shortcomings with the present technique. The optical equipment necessary to carry out this technique is typically expensive and requires trained staff to set it up and operate it. A significant amount of operator intervention is required to operate the apparatus, e.g. to focus the lens of the camera, to arrange even illumination of the artefact being imaged, and to change the wavelength filters. The apparatus needs to be housed in special premises, e.g. a dark room, because it is large and needs to operate in an environment devoid of external light and vibrations. Moreover, even with the most careful operation, because of the necessity to interchange parts, e.g. filters, between successive images being taken, it is difficult to achieve perfect alignment of successive images which tends to degrade the quality of the resulting multi-spectral image (which relies on alignment between corresponding pixels in the images taken at the different wavelengths). This in turn negates some of the potential benefit in analysing multi-spectral images.

The present invention aims to provide an improved technique and apparatus for carrying it out. When viewed from a first aspect the invention provides a method of capturing and processing a multi-spectral image of an object, comprising: placing said object on a flat-bed scanner, using said flat-bed scanner to illuminate the object successively with monochromatic light at a series of wavelengths to produce a plurality of images together forming a composite multi-spectral image, determining a spectral profile of at least a portion of said multi-spectral image and comparing said spectral profile to a stored spectral profile.

The invention also extends to an apparatus for capturing and processing a multi-spectral image of an object, comprising a flat bed scanner having: illumination means configurable to emit monochrome radiation at a plurality of different wavelengths: and detection means arranged to detect the intensity of the radiation reflected by the object and thereby produce an image of the object at each of said plurality of wavelengths; said apparatus further comprising means arranged to form a composite multi-spectral image from said images, and processing means arranged to determine a spectral profile of at least a portion of said multi-spectral image and compare said spectral profile to a stored spectral profile.

Thus it will be appreciated by those skilled in the art that the present invention provides a way of producing and analysing multi-spectral images of an object based on a flat-bed scanner. Flat bed scanners are generally compact, low in cost and easy to use in any location, environment or by any person, i.e. not necessarily only those who are highly qualified. Multiple scans at different wavelengths can be produced without moving the object between scans because the wavelength is changed by the monochrome radiation source which does not necessarily require any manual intervention or mechanical movement of the parts between the changes of wavelengths and because the object is fixed on the scanner's surface. Furthermore the monochrome radiation source can be remote and therefore made mechanically independent from the scanner thereby ensuring that any vibrations caused when changing the wavelength of the monochromatic radiation source are not transmitted to the scanner. The object and imaging apparatus can therefore remain still relative to one another resulting in perfect alignment of all the images at the different wavelengths, i.e. a certain pixel on all the images corresponds to a unique point on the object being imaged. This therefore allows for a fully-registered composite multi-spectral image to be produced which can be thought of as a 3D image map of the object with the x-y plane corresponding to the x-y coordinates of object, and the z-coordinate corresponding to the different wavelengths of the images.

By illuminating the object a plurality of times at the plurality of different monochromatic wavelengths, the object is only ever illuminated with the light intensity which is necessary for imaging. This contrasts with illuminating the object directly with a broadband white light source, which is then filtered after the light is reflected from the object, since the intensity of the source must then be great enough to give sufficient intensity at the specific wavelength of interest. The higher aggregate intensity gives rise to a greater risk of damage to fragile objects such as ancient artefacts.

The processing means provides enhanced visualisation of the different substances on an object, such as text or images applied to the substrate of the object, e.g. in ink, paint or pigment, as well as enhancing the contrast of this text or images from the substrate on which the ink, paint or pigment is disposed. This therefore allows degraded text or images, which would otherwise be invisible in conventional photography, or indeed photography using dedicated wavelengths, e.g. infrared, to be revealed.

In one set of embodiments the processing means is arranged to carry out a number of steps in order to provide enhanced visualisation of elements on the object, e.g. ink on papyrus. Following the scanning of the object at a number of different wavelengths, there exists, for each pixel on the image, an intensity of the reflected radiation for all the different wavelengths at which the object was scanned. This forms a three-dimensional multi-spectral image as explained above. The substrate of the object and the ink, pigment or paint, etc., used give different respective responses to different wavelengths of radiation.

Considering a given pixel or group of pixels, the information representing intensity at each of the wavelengths can be regarded as a spectral profile (equivalently "spectral signature"). In general these spectral profiles could be a superposition of the intensity responses from the ink, pigment or paint and the substrate, dependent on the amount of ink, pigment or paint, and the quality of the substrate (e.g. because of darkening or degradation) present across the area of the object covered by the pixel or group of pixels.

The processing means is arranged to analyse these spectral profiles and compare them to stored spectral profiles. This can enable the determination for each pixel or group of pixels of the composition of the corresponding part of the object if comparisons are made against the known spectral profiles of various possible materials present on the object, e.g. the substrate and inks, paints or pigments. Generally the spectral profile for a substrate will be different from the spectral profile for any ink, pigment or paint on the substrate.

In one set of embodiments a correlation coefficient is calculated for the spectral signature of each pixel or group of pixels either against the known spectral profiles of the ink or substrate materials—or, if these are unknown, against each possible match—e.g. for each of the possible materials for the substrate, ink, pigment or paint etc. Typically the correlation coefficient would have a value between 0 and 1, with the value increasing as the likelihood for the part of the image including the corresponding material increases. By plotting the correlation value for each pixel or group of pixels when compared to a given spectral profile (e.g. for a given ink hypothesis) a clearer image may be obtained showing where that ink etc. is present on the object. Of course if the material which a user is trying to distinguish from the substrate is unknown, it may be necessary to try a number of hypotheses and establish which gives the clearest image. This could be chosen visually or automatically. Alternatively a clearer part of the image could be selected by the user to act as a reference with the spectral profile of that part being used to compare against parts which are less clear.

To further refine the image, a threshold value for the correlation coefficient can be applied, with all the values below a certain threshold, e.g. in the range 0.85 to 0.95, being rejected as relating to background material, i.e. not the material for the hypothesis in question. The threshold value may be varied depending on the object or the hypothesis. The final image produced would be a binary image which can be used to study the position of a certain material on the object, e.g. to reveal writing in a certain ink on a document.

The processing means can also be arranged to generate feedback optimisation commands that refine the extraction of the image for a certain hypothesis. One possible way of doing this would be automatically to vary and optimise the threshold value. In an advantageous set of embodiments, feedback is used to select a reduced set of wavelengths that give the best results from an initial scan to be used for scanning subsequent objects of parts of an object. This speeds up subsequent scanning and processing without any loss of quality, especially if the objects are of similar type, e.g. on the same substrate and with the same ink, paint or pigment.

This arrangement of analysing the images produced by the scanner therefore enhances the contrast of the greyscale images, i.e. the raw intensity response data, to produce a clear image of a certain substance on an object. As this is just dependent on the spectral signature of each pixel, it is less sensitive to the amount of a certain substance present at each pixel on the object, because the spectral signature can be scaled to the necessary value to facilitate comparison with the known spectral profile according to the hypothesis in question.

Therefore it can be seen that the combination of the scanner with the processing means allows an object to be imaged at a number of wavelengths and subsequently enables the contrast between the substrate of the object, e.g. papyrus, to be enhanced and separated from the ink, paint or pigment on the substrate. The use of spectral profiles allows the identification and thus separation of different inks, paints or pigments, e.g. from different authors or dates, which were used on the substrate, and even allows images on the substrate which are very faint to be revealed as a clearly visible inscription.

As has been described previously for choosing different wavelengths at which to perform the scans, including having preset scanning functions, the processing means could also comprise different selectable features. This could include being able to select the threshold value for the correlation coefficient, or being able to select different versions of the procedure depending on the type of object or material being analysed. These selectable features could either be selectable on the scanner itself, e.g. as a set of buttons, or on the processing means, e.g. as a menu on a computer.

In preferred embodiments there is a direct data connection between the scanner and the processing means e.g. via a cable or by wireless communication to a computer, though embodiments are envisaged where the flat bed scanner incorporates dedicated processing means. However the inventors have appreciated that neither of these is essential and that, for example, the images taken by the detection means could be transferred to remote processing means e.g. by means of a data storage device such as a USB drive, or across a network to a remote computer. Alternatively the data could be stored either in the scanner or externally for subsequent processing.

Therefore when viewed from a second aspect the invention provides an apparatus for capturing a multi-spectral image of an object, comprising a flat bed scanner having: illumination means configurable to emit monochrome radiation at a plurality of different wavelengths; and detection means arranged to detect the intensity of the radiation reflected by the object and thereby produce an image of the object at each of said plurality of wavelengths; said apparatus being adapted to communicate, or store for subsequent processing, data corresponding to said images at each of said plurality of wavelengths.

The features discussed below are applicable to any of the previous aspects of the invention.

In a preferred set of embodiments the illumination means comprises a continuous strip illuminator, as is conventional in flat bed scanners, arranged as part of an optical assembly to move across the flat bed of the scanner thereby illuminating the whole of the object on the scanner.

The illumination means could comprise a plurality of light emitting diodes (LEDs); this would enable a number of different wavelength LEDs to be used to produce the monochrome radiation, with the LEDs of a certain wavelength being energised when the scan at that wavelength is performed. Alternatively the illumination means could comprise a broad band white source with a tunable liquid crystal filter or a monochromator. In a preferred set of embodiments however the illumination means comprises a broadband white light source which is passed through a wavelength bandpass filter. The wavelength bandpass filter may be of variable wavelength and arranged selectively to pass the required single monochromatic wavelength, or a plurality of different filters could be provided e.g. in the form of a filter wheel.

Thus in the preferred embodiments, the illumination means can be tuned to a certain monochromatic wavelength by choosing one filter from a plurality of filters each at different wavelengths through which to pass the broadband white light source. This enables the object to be illuminated and hence imaged at this particular monochromatic wavelength, and subsequently at a plurality of different wavelengths.

The illumination means could reside the same housing as the flat-bed of the scanner. For example in the set of embodiments that comprise a moving optical assembly, the light source could be disposed on the optical assembly. This might be suitable where the monochromatic light source comprises a plurality of LEDs, although the limited physical dimensions of the optical assembly might place a limit on the number of different wavelength LEDs that can be used. In a preferred set of embodiments however the illumination means comprises a monochromatic light source remote from the flat-bed of the scanner. This allows for as large a monochromatic light source as is necessary in order to generate the necessary plurality of monochromatic wavelengths. This set of embodiments makes it easier to provide a greater number of different wavelengths from the illumination means, as well as ensuring that any vibrations created from changing the wavelength of the radiation source are mechanically independent from the scanner and therefore are not propagated to the scanner.

Preferably the remote monochromatic light source is connected to the rest of the scanner via a fibre optic light guide. The fibre optic light guide could connect with a continuous strip illuminator, with the strip comprising the ends of the optical fibres in a line. The continuous strip illuminator could comprise a cylindrical lens through which the light emitted from the ends of the optical fibres is passed in order to focus the light onto the object on the scanner. The cylindrical lens could be fixed, or it could be arranged to move up and down in order to focus the light onto the surface of the scanned object.

The system could operate at a plurality of monochromatic wavelengths which were fixed, i.e. hardwired into the scanner with no means for changing or choosing the wavelengths used. This type of system could operate automatically, e.g. a start button is pressed and then all the scans at the predetermined wavelengths are taken and subsequently processed. Such operation might be suitable for a system which was repeatedly scanning similar documents that were all on the same substrate and had the same type of ink, paint or pigment on the substrate. However, this does not give any flexibility for using the system for any other use where it would be advantageous to be able to change or select the wavelengths used. Therefore in an alternative set of embodiments the system comprises means for controlling which wavelengths of radiation are used to illuminate the target object.

The adjustment means could comprise any suitable means for varying the wavelength of the monochromatic radiation source, and may be different depending on the type of monochromatic radiation source being used, particularly if the wavelengths available are at discrete, predetermined values (e.g. if the monochromatic radiation source comprises a plurality of LEDs of different wavelengths or a plurality of discrete filters), or able to be chosen from a continuous spectrum (e.g. if the monochromatic radiation source comprises a monochromator). Therefore a set of buttons, switches or an indexed dial may be suitable for a discrete wavelength source, and a continuous dial or slider may be suitable for a continuous wavelength source (these could either be hardware or software controls).

The system could be fully programmable with adjustment means as described above to select the wavelength for each individual scan and/or the system could be pre-programmed with a number of automatic functions, e.g. similar to the fully automatic system described above. Such a system could, for example, comprise a plurality of settings which when selected operated the scanner at a plurality of predetermined wavelengths. The settings could be selected by any suitable means, e.g. button(s), dial(s) or a touch screen on the scanner, or from a menu on a computer connected to the scanner. The settings would enable the scanner to be pre-programmed with a number of settings that were suitable for certain types of different objects, thereby enabling a user to easily produce a scan over a plurality of different wavelengths suitable for the object that they were interested in. This is because different objects are more effectively scanned at different sets of wavelengths to best reveal the text and/or images on them. The system may therefore comprise settings for objects with different substrates, e.g. papyrus, paper, and also with different inks, paints, or pigments. For example, iron ink is particularly visible in ultraviolet radiation and carbon ink is particularly visible in infrared radiation. Therefore if it is known that the object being scanned includes one of these inks, the user would want to include the associated wavelength in one of the plurality of different wavelengths that the scanner was operating at. The system may also comprise the ability to allow a user to create and store a new setting for a plurality of predetermined wavelengths.

In some embodiments the system could be operated at just a small number of different wavelengths, e.g. 3 or 6. In other sets of embodiments the system could be operated at a very large number of wavelengths, e.g. hundreds or thousands, making it hyper-spectral imaging. In a typical set of embodiments the wavelengths emitted by the monochromatic radiation source are arranged to be in the range from ultraviolet radiation to infrared radiation, e.g. 350 nm to 950 nm. However embodiments are envisaged in which the monochromatic radiation source is arranged to emit wavelengths across a much wider range of the electromagnetic spectrum including near-infrared range (NIR, 0.75-1.4 µm), short-wavelength infrared range (SWIR, 1.4-3 µm), mid-wavelength infrared range (MWIR, 3-8 µm), and long-wavelength infrared range (LWIR, 8-15 µm).

As well as preferably comprising a transparent, e.g. glass, plate on which the object to be scanned is placed, preferably the scanner also comprises a lid allowing flat objects to be held still on the scanner between the plate and the lid. Such a lid can also be arranged to block out light from the surroundings. This therefore means that it is not necessary to use the apparatus in a dark room to take the multi-spectral images as is necessary when using a multi-spectral camera, making its use more flexible.

The detection means for detecting the intensity of the monochrome radiation reflected by the object could be located in a stationary position in the scanner, with the reflected radiation being directed towards the detection means by use of mirrors and lenses if necessary. However in a preferred set of embodiments the detection means are located in the moving optical assembly. The detection means would then move along with the light source as the object is being scanned so that the light is reflected from the object directly back onto the detection means. As will be appreciated this enables high quality images to be taken as the distance between the artefact and the detection means is constant as the illuminator is moved across the scanner (at least for a flat object).

The detection means can comprise any suitable means which is able to register the intensity of the various wavelengths of radiation. One example would be an array of complementary metal-oxide-semiconductor (CMOS) chips, an array of charge-coupled devices (CCDs) or a contact image sensor (CIS). Another example would be focal plane arrays (FPA). CCD and CMOS sensors are preferred for visible and near-infrared imaging whereas FPAs are preferred for mid and long-wavelength infrared imaging.

As used herein, monochromatic radiation is defined as radiation at a certain wavelength with a spread of less than 20 nm at half intensity. In some embodiments however much narrower wavelength bands are used—e.g. with a half width of 10 nm or less. In some embodiments the radiation may have a half-width less than 5 nm.

While it is envisaged that the present invention will be primarily used to scan and produce multi-spectral images of historical documents, e.g. papyri and other artefacts, the invention is by no means just limited to such uses. Other objects which could be scanned using the present invention include paintings, drawings, photographs, fabrics, sculptures, pottery, relics, i.e. any object which has substances in or on it that could be revealed by multi-spectral imaging. The invention is also not limited to use with historical artefacts but can be used for present day objects. One particular use which is foreseen for the present invention is in modern forensic techniques where it could be used, for example, in detecting the forgery of official documents. Other envisaged application of this technology can be quality control in some manufactured items both of their substrate, such as paper, fabric, plastic, metal, wood, leather, rubber, etc., and of the layers of material covering the substrate, such as paint, varnish, protective and decorative coating, optical security features, etc. The technology can also be applied for multi-spectral and infrared examination of samples of biological and medical nature, such as plant leaves and animal or human skin, hair etc and other biologics.

Certain preferred embodiments of the invention will now be described, by way of example only, with reference to the accompanying drawings in which:

FIG. 2 shows a graph of spectral signatures for ink and papyrus.

Figure 1:
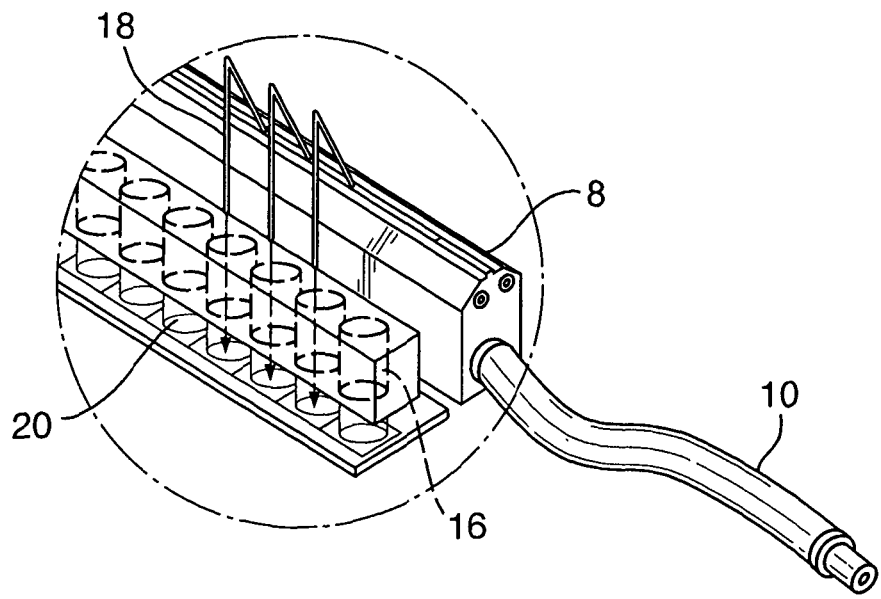
FIG. 1 shows of an embodiment in accordance with the present invention.
Figure 1:
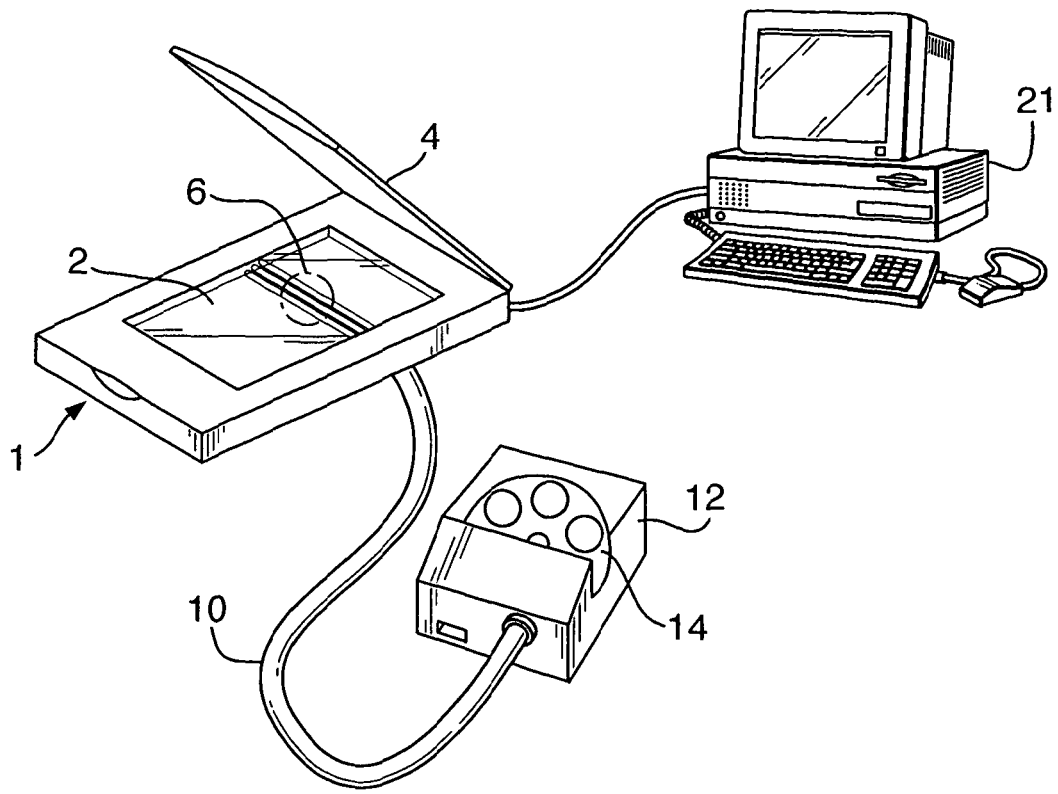

FIG. 1 shows a flat bed scanner 1 in accordance with the present invention. The scanner 1 comprises a glass plate 2 onto which objects such as documents can be placed to be scanned. The scanner 1 also has a lid 4 which can be closed on top of the object being scanned if it is flat (e.g. a document) to keep out any external light. An optical assembly 6 comprising a continuous strip illuminator 8 is arranged perpendicularly across the width of the scanner 1 and in use is translated move along the length of the scanner 1 in a known manner. The optical assembly 6 comprises a plurality of optical fibres which have their ends arranged in a line along the assembly.

The optical fibres together form a fibre optic light guide 10 for guiding light from a remote monochromatic radiation source 12 to the optical assembly 6.

The monochromatic radiation source 12 comprises a broadband white light source and a plurality of exchangeable monochromatic wavelength filters. One filter at a time is placed in front of the broadband white light source and then the subsequent filtered monochromatic radiation is fed into the plurality of optical fibres, from where it is directed down the light guide 10 to the continuous strip illuminator 8. The light source 12 is arranged to interchange the wavelength filters depending on the required scan to be performed. The different wavelength filters can be selected by adjusting a filter wheel 14.

The scanner 1 further comprises a plurality of lenses 16 which are arranged to focus light 18, emitted by the continuous strip illuminator 8 and reflected off the object being scanned, onto a plurality of image sensors 20. The image sensors are then arranged to send the data recorded to a computer 21 where the image can be analysed.

In operation, a document such as a papyrus with a faint inscription is placed onto the glass plate 2 of the flat bed scanner 1. The lid 4 of the scanner 1 is closed to block out all external light. The monochromatic wavelength at which the scan is to be performed is chosen by turning the filter wheel 14 on the illuminator 12 to the appropriate position under the control of the computer 21 (e.g. through a suitable control cable, not shown). The computer 21 may also determine the intensity of light to be provided by the illuminator 12. The filter wheel 14 acts to place the monochromatic wavelength filter for the desired wavelength in front of the broadband white light source. Monochromatic light is therefore sent down the light guide 10 through the optical fibres from the illuminator 12 to the continuous strip illuminator 8.

To perform the scan at the desired monochromatic wavelength, the optical assembly 6 moves from one end of the scanner 1 to the other, thereby illuminating and imaging all of the document on the glass plate 2 from below. The monochromatic light 18 emitted from the continuous strip illuminator 8 is reflected from the document and then passes through a plurality of lenses 16 which are arranged to focus the light 18 onto a plurality of image sensors 20. The image sensors 20 record the intensity of the light 18 reflected so that a greyscale image for that particular monochromatic wavelength can be produced.

This operation of scanning the document at a monochromatic wavelength is repeated at a plurality of different monochromatic wavelengths in order to produce the required number of images. As has been described previously, the scans can be taken at a different plurality of wavelengths depending on the type of document to be scanned, e.g. to be most efficient at revealing degraded text.

The image sensors 20 output their data to a computer 21 which combines the various images into a composite, three-dimensional multi-spectral image of the document. For each pixel on the images (corresponding to a unique position on the document) a spectral signature can be produced which gives the intensity of the reflected radiation at each monochromatic wavelength that was included in the scan. This spectral signature will be a superposition of the intensity responses from the different substances which are present in the part of the document covered by the pixel, for example ink and papyrus.

FIG. 2 shows spectral signatures for ink 22 and papyrus 24 (i.e. a section of papyrus with no ink), for scans at a plurality of different wavelengths between 365 nm and 940 nm. Therefore it can be seen that the ink 22 and papyrus 24 have very different spectral signatures, with the ink 22 reflecting a high fraction of the incident radiation at short wavelengths, and a low fraction at long wavelengths. In contrast the papyrus 24 reflects a low fraction of the incident radiation at short wavelengths, and a high fraction at long wavelengths. These different spectral signatures for the ink 22 and papyrus 24 can therefore be used to analyse the multi-spectral images of the document in order to extract any faded text written in ink on the document.

The spectral signature at each pixel is compared to the known spectral signatures for ink, and possibly also for papyrus, and a correlation coefficient is calculated for each pixel. If the ink is known a single known spectral signature corresponding to the ink may be used. If the ink is not known, several known profiles may be compared to try to achieve the best match. The calculation of the correlation coefficient returns a value between 0 and 1 where a high value indicates that the likelihood for a pixel to include a certain substance is high, and conversely a low value indicates that the likelihood for a pixel to include a certain substance is low.

Once the correlation coefficient has been calculated for the spectral signature of the pixel, a threshold e.g. of 0.9 is applied to the correlation coefficient, i.e. if the correlation coefficient is below 0.9 that pixel is treated as having no ink and if it is above 0.9 the pixel is treated as having ink on it. An image is thereby produced plotting which pixels have ink and which don't. This can be repeated for each candidate ink if appropriate until the clearest image is achieved. The image produced using this method enables ink patterns which were not necessarily visible, because of fading, degradation, dirt, light exposure, etc, to be revealed through analysis of the spectral signatures which make up the multi-spectral image.

It will be appreciated by those skilled in the art that only a small number of possible embodiments have been described and that many variations and modifications are possible within the scope of the invention. For example the monochromatic radiation source 12 need not comprise a set of interchangeable wavelength filters, but could be, for example, a white light source with a tunable liquid crystal filter or a monochromator, or a set of LEDs of different wavelengths. A monochromator, controlled e.g. by the computer 21 as in the described embodiment, can provide the choice of any monochromatic wavelength within a continuous spectrum of radiation. Any suitable data processing means to analyse the multi-spectral images could be used, either as part of the same apparatus or remote from the apparatus.

The invention claimed is:

1. A method of capturing and processing a multi-spectral image of an object, comprising: placing said object on a flat-bed scanner, using said flat-bed scanner to illuminate the object successively with monochromatic light from a monochromatic light source remote from the flat-bed scanner at a series of wavelengths to produce a plurality of images together forming a composite multi-spectral image, determining a spectral profile of at least a portion of said multi-spectral image, and comparing said spectral profile to a stored spectral profile, wherein said step of comparing said spectral profile to a stored spectral profile comprises calculating a correlation coefficient for the spectral profile of each pixel or group of pixels on the multi-spectral image according to a hypothesis for the pixel or group of pixels including a material.

2. A method as claimed in claim 1 comprising applying a threshold value to the correlation coefficient and accepting the hypothesis if the value of the correlation coefficient is greater than the threshold value.

3. A method as claimed in claim 2 comprising forming a binary image displaying all pixels or groups of pixels with a correlation coefficient greater than the threshold value for a certain hypothesis.

4. A method as claimed in claim 3 comprising generating feedback optimization commands to refine the binary image.

5. A method as claimed in claim 4 comprising performing an initial scan, and selecting a reduced number of wavelengths for subsequent scans.

6. An apparatus for capturing and processing a multi-spectral image of an object, comprising a flat-bed scanner including: an illumination arrangement configured to illuminate the object successively with monochromatic light at a series of wavelengths, wherein the illumination arrangement is optically coupled to a monochromatic light source remote from the flat-bed scanner, and the monochromatic light source is configured to emit monochrome radiation at a plurality of different wavelengths; and a detector arranged to detect the intensity of the radiation reflected by the object and thereby produce an image of the object at each of said plurality of wavelengths; said apparatus further comprising an arrangement to form a composite multi-spectral image from said images, and a processor arranged to determine a spectral profile of at least a portion of said multi-spectral image and compare said spectral profile to a stored spectral profile, wherein the processor is arranged to calculate a correlation coefficient for the spectral profile of each pixel or group of pixels on the multi-spectral image according to a hypothesis for the pixel or group of pixels including a material.

7. An apparatus as claimed in claim 6 wherein the processor is arranged to apply a threshold value to the correlation coefficient and accept the hypothesis if the value of the correlation coefficient is greater than the threshold value.

8. An apparatus as claimed in claim 7 wherein the processor is arranged to form a binary image displaying all pixels or groups of pixels with a correlation coefficient greater than the threshold value for a certain hypothesis.

9. An apparatus as claimed in claim 8 wherein the processor is arranged to generate feedback optimization commands to refine the binary image.

10. An apparatus as claimed in claim 9 wherein the flat-bed scanner is arranged to perform an initial scan, and the processor is arranged to select a reduced number of wavelengths for use in subsequent scans.

11. An apparatus as claimed in claim 6 comprising a direct data connection between the scanner and the processor.

12. An apparatus as claimed in claim 6 wherein the illumination arrangement comprises a continuous strip illuminator.

13. An apparatus as claimed in claim 6 wherein the illumination arrangement comprises a broadband white light source which is passed through a wavelength bandpass filter.

14. An apparatus as claimed in claim 6 wherein the remote monochromatic light source is connected to at least a portion of the scanner via a fiber optic light guide.

15. An apparatus as claimed in claim 6 comprising a controller for controlling which wavelengths of radiation are used to illuminate the target object.

16. An apparatus as claimed in claim 6 wherein the wavelengths emitted by the monochromatic radiation source are arranged to be in a range from 350 nm to 15 μm.

17. An apparatus as claimed in claim 6 wherein the flat-bed scanner comprises a transparent plate.

18. An apparatus as claimed in claim 6 wherein the flat-bed scanner comprises a lid.

19. An apparatus as claimed in claim 6 wherein the illumination arrangement comprises a moving optical assembly.

20. An apparatus as claimed in claim 19 wherein the detector is located in the moving optical assembly.

21. An apparatus as claimed in claim 6 wherein the detector comprises an array of complementary metal-oxide-semiconductor (CMOS) chips, an array of charge-coupled devices (CCDs), a contact image sensor (CIS) or a focal plane array (FPA).

* * * * *